United States Patent
Arrivo et al.

(10) Patent No.: US 7,400,400 B2
(45) Date of Patent: Jul. 15, 2008

(54) METHOD FOR MONITORING PARTICLE SIZE

(75) Inventors: Steven M. Arrivo, Ann Arbor, MI (US); William E. Bowen, Ambler, PA (US); Robert A. Reed, Line Lexington, PA (US); John P. Higgins, Lansdale, PA (US)

(73) Assignee: Merck & Co. Inc., Rahway, NJ (US)

( * ) Notice: Subject to any disclaimer, the term of this patent is extended or adjusted under 35 U.S.C. 154(b) by 305 days.

(21) Appl. No.: 10/488,604

(22) PCT Filed: Aug. 23, 2002

(86) PCT No.: PCT/US02/26775

§ 371 (c)(1),
(2), (4) Date: Sep. 20, 2004

(87) PCT Pub. No.: WO03/021213

PCT Pub. Date: Mar. 13, 2003

(65) Prior Publication Data

US 2005/0018188 A1    Jan. 27, 2005

Related U.S. Application Data

(60) Provisional application No. 60/316,073, filed on Aug. 29, 2001.

(51) Int. Cl.
*G01N 21/00* (2006.01)
(52) U.S. Cl. ...................... 356/342; 356/337
(58) Field of Classification Search ............... 356/335, 356/336, 337, 338, 339, 340, 341, 342
See application file for complete search history.

(56) References Cited

U.S. PATENT DOCUMENTS

| | | | |
|---|---|---|---|
| 3,640,627 A | 2/1972 | Beattie et al. | |
| 3,817,628 A | 6/1974 | Adams | |
| 4,260,258 A | 4/1981 | Rose et al. | |
| 4,842,406 A | 6/1989 | VonBargen | |
| 4,969,741 A * | 11/1990 | Kennedy et al. | 356/338 |
| 5,061,070 A | 10/1991 | Batchelder et al. | |
| 5,343,044 A | 8/1994 | Sjaunja et al. | |
| 5,633,503 A | 5/1997 | Kosaka | |
| 5,710,069 A | 1/1998 | Farkas et al. | |
| 5,818,583 A | 10/1998 | Sevick-Muraca et al. | |
| 6,049,082 A | 4/2000 | Methfessel | |
| 6,119,510 A | 9/2000 | Carasso et al. | |
| 6,177,983 B1 | 1/2001 | Trainer | |
| 6,211,956 B1 | 4/2001 | Nicoli | |
| 6,246,474 B1 | 6/2001 | Cerni et al. | |
| 6,263,725 B1 | 7/2001 | Garver et al. | |
| 6,600,559 B2 * | 7/2003 | Switalski et al. | 356/336 |
| 6,660,995 B1 * | 12/2003 | Canpolat et al. | 250/227.23 |
| 6,917,424 B2 * | 7/2005 | Rodrigues et al. | 356/326 |

* cited by examiner

*Primary Examiner*—Roy M Punnoose
(74) *Attorney, Agent, or Firm*—J. Eric Thies; William Krovatin

(57) ABSTRACT

The present invention provides methods for the use of visible and/or near-infrared spectroscopic methodology to monitor and control processes for the generation of particles, including processes that provide for a reduction in particle size and processes that result in an increase in particle size. One embodiment of the present invention employs visible and/or near-infrared diffuse reflectance spectroscopy to monitor particle size. The present invention is particularly useful for monitoring particle size of optically dense samples and is further useful for monitoring the endpoint of particle generation processes. In contrast to methods known in the art, the present invention is especially useful for on-line monitoring of particle size.

17 Claims, 1 Drawing Sheet

METHOD FOR MONITORING PARTICLE SIZE

CROSS REFERENCE TO RELATED APPLICATIONS

This application is a U.S. National Phase application under 35 U.S.C. § 371 of PCT Application No. PCT/US02/26775, filed Aug. 23, 2002, which claims priority under 35 U.S.C. § 119 from U.S. application No. 60/316,073 filed Aug. 29, 2001.

BACKGROUND OF THE INVENTION

The present invention relates to methods for monitoring particle size during chemical operations. Particle size monitoring is employed in a wide variety of pharmaceutical and chemical development and manufacturing programs.

The methods known in the art for determining particle size are laborious, time consuming and potentially inaccurate. In general, samples are obtained from the processing equipment, transported to another building/facility and analyzed. Dilutions of approximately 1000 fold are first necessary, and then the samples are "particle sized" such as by laser light scattering with a Coulter LS230 or a Horiba LA-910 commercial particle size instrument. This instrument reports a mean particle size and D90 values (a size of which 90% of the particles are less than this value). The use of the Coulter LS230 requires sampling from the process stream, delivery of sample to an analytical laboratory, significant dilution of the sample and then approximately an additional 30 minutes to generate results. The overall process can take up to an hour, raises concerns about the integrity of the sample generated, and does not provide real time feedback for process monitoring or control. The imitations of methods known in the art include difficulties of off line monitoring, laborious process, physical distance between process and analytic laboratory, non-homogeneities in samples, dilution effects, unrepresentative sample collection, changes in the sample over time and the lag time in processing while waiting for the analysis.

The present invention overcomes the limitations of methods known in the art such as those which employ the Coulter LS230 instrument (or similar methodology). Moreover, in contrast to previously known methods, the present invention results in improved sensitivity to changes in the process near the end of the process cycle. The ultimate utilization of this monitoring scheme can allow the operator to terminate the process operation when the particles have reached the desired size distribution as soon as that condition is reached. The improved efficiency will allow more effective use of processing time, resulting in reductions of manufacturing cycle times to be realized over the manufacturing life cycle of any chemical product that is prepared utilizing such technology.

SUMMARY OF THE INVENTION

The present invention provides methods for the use of visible and/or near-infrared spectroscopic methodology to monitor and control processes for the generation of particles, including processes that provide for a reduction in particle size and processes that result in an increase in particle size. One embodiment of the present invention employs visible and/or near-infrared diffuse reflectance spectroscopy to monitor particle size. The present invention is particularly useful for monitoring particle size of optically dense samples and is also useful for monitoring the endpoint of particle generation processes. In contrast to methods known in the art, the present invention is well suited for the on-line monitoring of particle size.

DETAILED DESCRIPTION OF THE INVENTION

Figure 1:
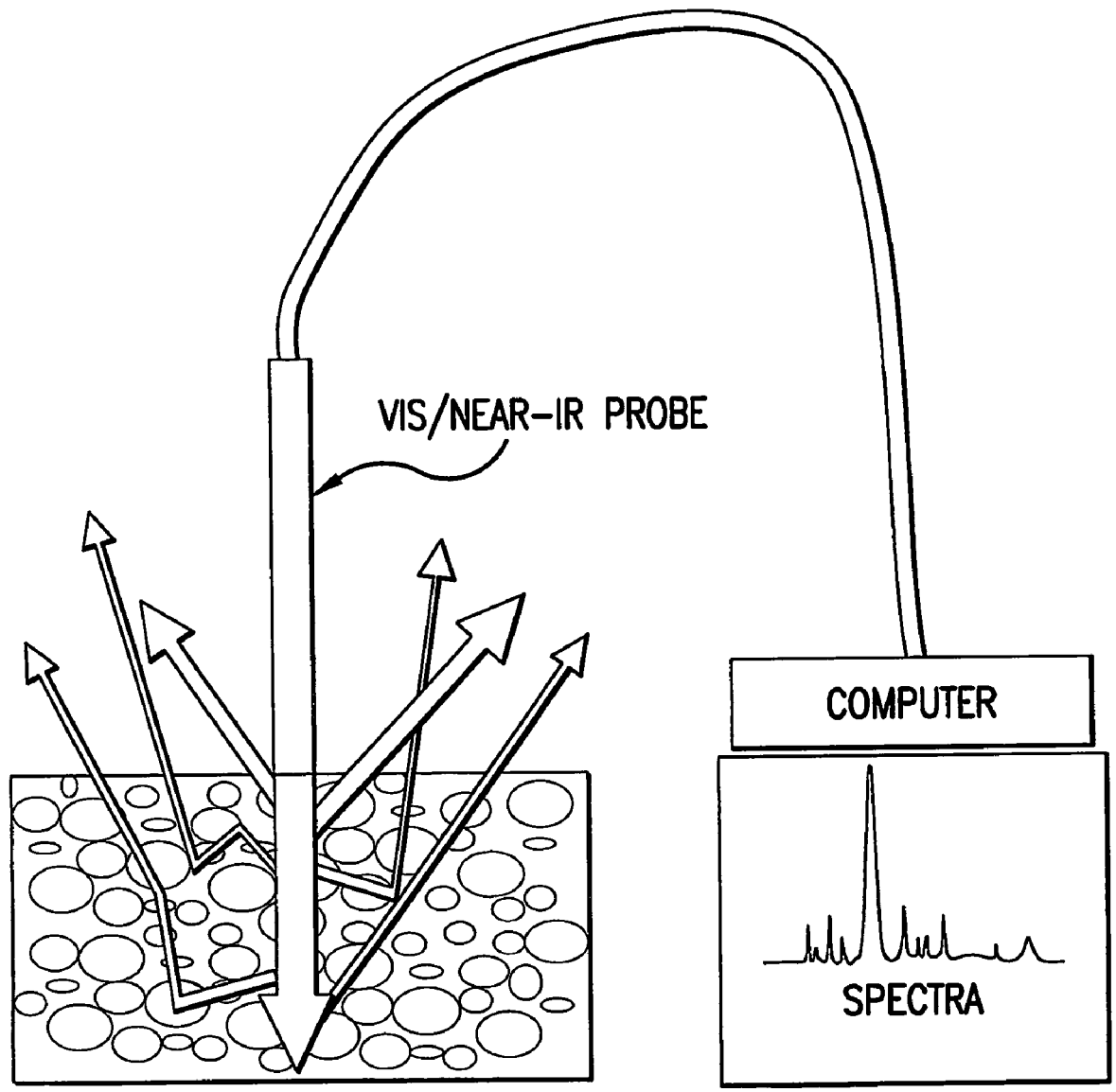
FIG. 1 shows a basic system for particle size monitoring. As depicted in FIG. 1, spectroscopic data may be collected in a diffuse reflectance backscattered configuration. A visible and/or near-infrared spectroscopic probe is employed to collect diffuse reflectance spectra from a suspension of particles. Such spectra may be collected over time thereby monitoring changes in the size of the particles.

The present invention is directed to methods for the use of visible and/or near-infrared spectroscopic methodology to monitor and control processes for the generation of particles, including processes that provide for a reduction in particle size and processes that result in an increase in particle size.

An embodiment of the present invention relates to the use of visible and near-infrared spectroscopic methodology to monitor and control slurry milling processes that reduces the particle size of high concentration solid substances from the size range of >100 microns to the submicron size range. In an embodiment of the present invention the size of the particles changes within the range of 100 microns to 200 nm. In the present invention the size of the particles may also be in the range of 100 microns to 1 micron. This present invention is particularly useful in wet media milling processes.

Another embodiment of the present invention relates to the use of visible and near-infrared spectroscopic methodology to monitor particle size growth in the sub-micron to the micron size range. In this embodiment, the present invention is utilized to monitor particle size in operations where the particle size is increasing instead of decreasing. Such process include the generation of particles by fermentation, aglomeration, aggregation and the like.

An embodiment of the present invention is directed to a method for monitoring the change in size of particles in a solvent during a process to generate such particles that comprises:
  (a) obtaining a first visible and/or near-infrared diffuse reflectance spectra of the particles in the solvent at an initial time point;
  (b) obtaining a second visible and/or near-infrared diffuse reflectance spectra of the particles in the solvent at a later time point;
  (c) comparing the first visible and/or near-infrared diffuse reflectance spectra to the second visible and/or near-infrared diffuse reflectance spectra to monitor the change in size of the particles.

Another embodiment of the present invention is directed to a method for monitoring the change in size of particles in a solvent during a process to generate such particles that comprises:
  (a) obtaining visible and/or near-infrared diffuse reflectance spectra for a plurality of reference samples of particles in the solvent wherein the particles in each reference sample possess a known size;
  (b) obtaining a visible and/or near-infrared diffuse reflectance spectra of the particles in the solvent during the process to generate the particles;
  (c) comparing the spectra from the process to generate the particles to the spectra for the plurality of reference samples;

(d) identifying which of the spectra for the plurality of reference samples most closely matches the spectra from the process to generate the particles, thereby correlating the known size of the particles in the reference sample to the size of the particles resulting from the process to generate the particles;

(e) repeating steps (a)-(d) until the particles resulting from the process to generate the particles have reached the desired size.

Another embodiment of the present invention is directed to a method for determining when the size of particles in a solvent has reached a steady state during a process to generate such particles that comprises:

(a) obtaining a first visible and/or near-infrared diffuse reflectance spectra of the particles in the solvent at an initial time point;

(b) obtaining a second visible and/or near-infrared diffuse reflectance spectra of the particles in the solvent at a later time point;

(c) comparing the first visible and/or near-infrared diffuse reflectance spectra to the second visible and/or near-infrared diffuse reflectance spectra; and (d) repeating steps (a)-(c) until there are no significant differences between the first visible and/or near-infrared diffuse reflectance spectra and the second visible and/or near-infrared diffuse reflectance spectra.

In an embodiment of the invention, visible and/or near infrared spectroscopic data are collected in a diffuse (or diffusal) reflectance mode, preferably in a diffuse reflectance backscattered configuration. While not being limited to a specific theory of operation, the inventors believe that the optically thick or dense suspension of solids provides scattering centers for the photons and allows them to return to the fiber optic probe and be detected. Alternatively, spectroscopic data are collected by employing transmission visible/near-infrared spectroscopy. When employing transmission spectroscopy the appropriate path length is dependent upon the concentration of particles in the suspension.

In the present invention, visible and/or near-infrared spectra are collected directly on the substance which is undergoing the particle generating operation to predict the particle size with respect to the mean, D90, or other descriptors as desired.

In a specific embodiment of the present invention, a spectrum is collected from a suspension of particles over the desired visible and/or near-infrared wavelength range (such as from 400 nm to 2500 nm) to obtain a spectral signature or snapshot at specific time point(s) throughout the operation that reduces or increases particle size. This spectrum is then correlated to a particle size parameter of interest (such as mean or D90) using standard chemometric techniques, such as those that involve the frequency range of 400-1850 nm. A preferred wavelength for monitoring particle size in water is about 1460 nm. For suspensions containing particles that are larger than the wavelength of visible/near infrared light, the absorbance will decrease with increasing particle size and increase with decreasing particle size. For suspensions containing particles that are smaller than the wavelength of the visible/near infrared light, the absorbance in the visible and/or near-infrared spectrum decreases with increasing particle size and increases with decreasing particle size.

To provide robustness and accuracy of the method, a set of spectra may be correlated to a set of particle size descriptors from as many operations as possible. Alternatively, changes in particle size during particle size reduction or increase may be monitored without calibration by examining the trend of the maximum absorbance for a given spectral band.

In many applications, the raw spectral data is of high enough quality to monitor the peak absorbance of one or more spectral bands to determine operation end point. This methodology does not furnish particle size descriptors, but allows the particle generation operation to be shut down at the appropriate time.

In a preferred embodiment, the present invention provides methods to measure particle size during a unit operation to determine when the desired endpoint has been reached.

The present invention may be employed for real time on-line determination of particle size in solid suspensions. This methodology can also be used to monitor the progress of the particle size reduction or growth unit operation, with or without quantitative calibrations. In such on-line methods, the probe directly contacts the particle suspension during the process.

In a preferred embodiment, the present invention may be employed for on-line or continuous monitoring of particle size in processes for particle generation, such as when the particle generation is conducted in a closed-loop fashion.

In one aspect of the present invention, a probe is employed to measure particle size with undiluted, continuous, on-line sampling for real time process control. The probe includes a source of visible and/or infrared illumination and a detector system. Optionally, a computer or microprocessor receives signals from the detector and performs a particle size measurement.

The present invention may be utilized to monitor the size of particles that are dispersed or suspended in any solvent system, but it is expected to find its greatest application in processes wherein the solvent comprises water, such as full or partially aqueous systems.

Because the present invention employs visible and/or near-infrared spectroscopic methodology to monitor the amount of water absorption, the tool is sensitive to only physical properties in this regime and has general applicability to monitoring the particle generation of any solid chemical compound, such as a pharmaceutical, chemical, abrasive, ceramic, pigment, and the like where particle size affects the quality of the manufactured product.

The present invention correlates to the physical characteristics of the chemical compound and thus has general applicability to particle generation of any organic or inorganic chemical compound.

The present invention has particular applicability to particle generation of a pharmaceutical compound.

In the present invention the particles are present at concentration such that a spectrum may collected over the desired visible and/or near-infrared wavelength range. When employing a diffuse reflectance backscattered configuration, it is preferred that particles are present at a concentration of 2-50% solids, preferably 5-45% solids, more preferably 7-40% solids, and even more preferably about 30% solids. In general, diffuse reflectance may be employed for optically dense samples of greater than about 5% solids. When employing transmission visible and/or near-infrared spectroscopy it is preferred that particles are present at a concentration of less than 20% solids. As used herein, "particles" refers to the solids or crystals that are present in the solvent. The particles which are present in the solvent may be characterized as a suspension, colloidal dispersion, and the like.

In a specific embodiment of the present invention, visible and/or near-infrared spectra are obtained for samples of varying particle sizes wherein the particle size is determined by conventional methods, then such spectra are compared to the spectra which is obtained from monitoring during the particle generation processes.

In an embodiment of the present invention, visible and/or near-infrared spectroscopic data is obtained for off-line samples of particle suspensions, then standard chemometric techniques are employed to establish a correlation of the spectra with particle size. Either transmission or diffuse reflectance is employed as appropriate for data collection. On-line visible and/or near-infrared spectroscopic data is collected during unit operation and the spectra from the on-line data is correlated with the primary particle size data from samples pulled during unit operation. Optionally, control of the operation may be possible without calibration.

In a preferred embodiment of the present invention, a typical particle size reduction unit operation is conducted as follows. A visible and/or near-infrared spectroscopic probe is employed to collect diffuse reflectance spectra from a suspension of particles and the raw peak absorbance value from any of several visible and/or near-infrared absorbance bands is used to determine when changes to raw spectra have stopped. Optionally, an algorithm which examines the change in absorbance provides feedback to a control unit to automatically stop unit operation when the particle size has reached the desired steady state.

In a preferred embodiment of the present invention, a typical particle size growth unit operation is similarly conducted as follows. A visible and/or near-infrared spectroscopic probe is employed to collect diffuse reflectance spectra from a suspension of particles and the raw peak absorbance value from any of several visible and/or near-infrared absorbance bands is used to determine when changes to raw spectra have stopped. Optionally, an algorithm which examines the change in absorbance provides feedback to a control unit to automatically stop unit operation when the particle size has reached the desired steady state.

The accuracy and precision of the present method are consistent with methods known in the art such as the laser light scattering primary method. Moreover, the present invention provides significant advantages over methods known in the art include robustness and ruggedness are improved with increased data collection, dilution is not required, non-destructive, suitable for process monitoring, avoids sampling issues (e.g. inhomogeneous samplings), provides real time process feedback, can be used for both on-line and at-line analyses, high enough precision for end point determination The methodology of the present invention is quite different than existing technologies. For example, it exploits the property of light scattering by optically thick samples. All other light scattering techniques need very dilute samples to theoretically describe the scattering and calculate particle size distributions. The present invention operates outside the classical scattering regime which requires low particle concentration. The relatively high particle concentration provides the ability to monitor the physical changes to the particle size by increasing the effective path length the photon travels in the scattering medium. The methodology of the present invention has been demonstrated to provide a very sensitive means to detect changes in particle size. In fact, the method is so sensitive that in certain situations it is possible to detect changes in the D90 on the order of 1-2 nm (as validated by off-line Coulter LS-230 laser light scattering).

Many of the apparatus and materials employed in the present invention are either commercially available or known in the literature and others can be prepared following literature methods described for analogous apparatus and materials.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, process conditions other than the particular conditions as set forth herein above may be applicable as a consequence of variations in the methodology or apparatus employed to practice the invention indicated above. Likewise, the may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for monitoring the change in size of particles in a solvent during a process to generate such particles that comprises:
   (a) obtaining a first near-infrared diffuse reflectance spectra in a diffuse reflectance backscattered configuration of the particles in the solvent at an initial time point;
   (b) obtaining a second near-infrared diffuse reflectance spectra in a diffuse reflectance backscattered configuration of the particles in the solvent at a later time point;
   (c) comparing the first near-infrared diffuse reflectance spectra to the second near-infrared diffuse reflectance spectra to monitor the change in size of the particles, wherein the monitoring of the change in size of the particles is used to control the process to generate such particles.

2. The method of claim 1 for monitoring the change in size of particles of a pharmaceutical compound in a solvent during a process to generate such particles.

3. The method of claim 1 wherein the near infrared spectroscopic data are collected at a wavelength of about 1460 nm.

4. The method of claim 1 wherein the solvent comprises water.

5. The method of claim 1 wherein the monitoring of the change in size of particles is employed for on-line or continuous monitoring of particle size in a process for particle generation.

6. The method of claim 1 wherein the size of the particles changes within the range of 100 microns to 200 nm.

7. A method for monitoring the change in size of particles in a solvent during a process to generate such particles that comprises:
   (a) obtaining near-infrared diffuse reflectance spectra in a diffuse reflectance backscattered configuration for a plurality of reference samples of particles in the solvent wherein the particles in each reference sample possess a known size;
   (b) obtaining near-infrared diffuse reflectance spectra in a diffuse reflectance backscattered configuration of the particles in the solvent during the process to generate the particles;
   (c) comparing the spectra from the process to generate the particles to the spectra for the plurality of reference samples;
   (d) identifying which of the spectra for the plurality of reference samples most closely matches the spectra from the process to generate the particles, thereby correlating the known size of the particles in the reference sample to the size of the particles resulting from the process to generate the particles, wherein correlating the known size of the particles in the reference sample to the size of the particles resulting from the process to generate the particle is used to control the process to generate such particles;

(e) repeating steps (a)-(d) until the particles resulting from the process to generate the particles have reached the desired size.

8. The method of claim 7 wherein the near infrared spectroscopic data are collected at a wavelength of about 1460 nm.

9. The method of claim 7 wherein the solvent comprises water.

10. The method of claim 7 wherein the monitoring of the change in size of particles is employed for on-line or continuous monitoring of particle size in a process for particle generation.

11. The method of claim 7 wherein the size of the particles changes within the range of 100 microns to 200 nm.

12. A method for determining when the size of particles in a solvent has reached a steady state during a process to generate such particles that comprises:

(a) obtaining a first near-infrared diffuse reflectance spectra in a diffuse reflectance backscattered configuration of the particles in the solvent at an initial time point;

(b) obtaining a second near-infrared diffuse reflectance spectra in a diffuse reflectance backscattered configuration of the particles in the solvent at a later time point;

(c) comparing the first near-infrared diffuse reflectance spectra to the second near-infrared diffuse reflectance spectra; and (d) repeating steps (a)-(c) until there are no significant differences between the first near-infrared diffuse reflectance spectra and the second near-infrared diffuse reflectance spectra, wherein the foregoing steps are used to control the process to generate such particles.

13. The method of claim 12 for determining when the size of particles of a pharmaceutical compound in a solvent has reached a steady state during a process to generate such particles.

14. The method of claim 12 wherein the near infrared spectroscopic data are collected at a wavelength of about 1460 nm.

15. The method of claim 12 wherein the solvent comprises water.

16. The method of claim 12 wherein the monitoring of the change in size of particles is employed for on-line or continuous monitoring of particle size in a process for particle generation.

17. The method of claim 12 wherein the size of the particles changes within the range of 100 microns to 200 nm.

* * * * *